United States Patent [19]

Hammer et al.

[11] Patent Number: 5,738,676
[45] Date of Patent: Apr. 14, 1998

[54] LASER SURGICAL PROBE FOR USE IN INTRAOCULAR SURGERY

[76] Inventors: Daniel X. Hammer, 5122 Crusade, San Antonio, Tex. 78218; Cynthia A. Toth, 928 Pinehurst Dr., Chapel Hill, N.C. 27514; William P. Roach, 5622 Evers Rd. Apt. 2808, San Antonio, Tex. 78238; Gary D. Noojin, 308 Mountain Shadows, San Antonio, Tex. 78233

[21] Appl. No.: 367,602

[22] Filed: Jan. 3, 1995

[51] Int. Cl.$^6$ .................. A61B 17/32; A61B 17/36
[52] U.S. Cl. ............................... 606/4; 606/17
[58] Field of Search .................. 606/4, 5, 6, 10, 606/12, 14, 15, 16, 17

[56] References Cited

U.S. PATENT DOCUMENTS

| | | | |
|---|---|---|---|
| 4,445,892 | 5/1984 | Hussein et al. | 606/15 |
| 4,753,510 | 6/1988 | Sezerman | 350/96.21 |
| 4,865,029 | 9/1989 | Pankratov et al. | 606/7 |
| 4,889,406 | 12/1989 | Sezerman | 350/96.21 |
| 4,963,143 | 10/1990 | Pinnow | 606/17 |
| 5,053,033 | 10/1991 | Clarke | 606/3 |
| 5,222,952 | 6/1993 | Loertscher | 606/15 |
| 5,246,435 | 9/1993 | Bille et al. | 606/6 |
| 5,257,989 | 11/1993 | Celaya et al. | 606/6 |
| 5,263,950 | 11/1993 | L'Esperance, Jr. | 606/6 |
| 5,290,272 | 3/1994 | Burstein et al. | 606/4 |
| 5,318,560 | 6/1994 | Blount et al. | 606/4 |
| 5,336,215 | 8/1994 | Hsueh et al. | 606/4 |
| 5,411,500 | 5/1995 | Lafferty et al. | 606/14 |
| 5,495,541 | 2/1996 | Murray et al. | 606/17 |

OTHER PUBLICATIONS

Cleary, Intra-Ocular Laser Probe (ILSP) for Vitreous Micro-Surgery, Unpublished Final Report for Graduate Student Research Program, Univ. of Alabama at Birmingham, pp.6-1 –6-20, Aug.; 1994.

Toth et al., Gradient Index(GRIN) Lens Multimode Fiber Probe for Laser Induced Breakdown in the Eye, Proceedings of Ophthalmic Technologies IV, vol. 2126, pp. 291–304, 1994.

Rol et al., Q–Switched Pulses and Optical Breakdown Generation Through Optical Fibers, Laser and Light In Ophthalmology, vol. 3, No. 3, pp. 213–219, 1990.

Meyers et al., Phototransection of Vitreal Membranes With the Carbon Dioxide Laser in Rabbits, Ophthalmology, vol. 90, No. 5, pp. 563–568, May 1983.

Gitomer et al., Laser–Produced Plasmas in Medicine, IEEE Transactions on Plasma Science, vol. 19, No. 6, pp. 1209–1219, Dec. 1991.

(List continued on next page.)

*Primary Examiner*—John P. Lacyk
*Assistant Examiner*—Sonya Harris-Ogugua
*Attorney, Agent, or Firm*—Fredric L. Sinder; Thomas L. Kundert

[57] ABSTRACT

A novel microfocusing laser surgical probe for use in intraocular surgery combines a high power laser with a gradient index (GRIN) lens to provide sufficient energy density at a focal point inside the eye to achieve laser induced breakdown and destroy fibrovascular membranes resulting from diabetes and other diseases. The gradient index lens steeply focuses the light close to its end so that the energy density of the light widely diverges beyond the focal point to reduce the potential for damage to the underlying retina. The gradient index lens also focuses the light far enough from the end of the lens to prevent damage to the lens itself. In a first embodiment, an open transmission line couples a YAG laser to a gradient index lens so that the light is still collimated when it strikes the lens. This first probe may be articulated by the use of mirrors or other optical devices. In a second embodiment, a tapered optical fiber couples a YAG laser to a gradient index lens to increase the maneuverability of the probe. An air gap separates the end of the optical fiber from the lens to better couple the light energy output from the optical fiber to the lens.

6 Claims, 2 Drawing Sheets

OTHER PUBLICATIONS

Decker–Dunn et al., Multifiber Gradient–Index Lens laser Angioplasty Probe, Lasers in Surgery and Medicine, vol. 10, pp. 85–93, 1990.

Margolis et al., Erbium–Yag Laser Surgery on Experimental Vitreous Membranes, Archieves of Ophthalmology, vol. 101, pp. 424–428, 1989.

Pankratov et al., A Step–Zoom Probe For Laser Endophotocoagulation:I. Design, Ophthalmic Surgery, vol. 18, No. 1, pp. 61–65, Jan. 1987.

LASER SURGICAL PROBE FOR USE IN INTRAOCULAR SURGERY

RIGHTS OF THE GOVERNMENT

The invention described herein may be manufactured and used by or for the Government of the United States for all governmental purposes without the payment of any royalty.

BACKGROUND OF THE INVENTION

The present invention relates generally to eye surgery, and more specifically to the surgical removal of fibrovascular membranes from within the vitreous cavity of the eye.

Fibrovascular membranes and vitreous strands result from severe proliferative diabetic retinopathy and similar proliferative retinopathies. Current surgical techniques for removing such membranes involve cutting the membranes with microscissors or other micro-cutting devices. Despite significant advances in instruments and techniques, the mechanical movement of scissors blades or aspirating-cutting systems can damage adjacent tissues either directly or by shearing and traction. Shearing and traction can cause retinal detachment. Moreover, cutting instruments need to be placed underneath a membrane in order to cut it.

Lasers are frequently used for intraocular (i.e., inside the eye) surgery, but their use has generally been limited to the use of low power lasers as a thermal source for photocoagulation or laser angioplasty. Several laser techniques using high power lasers have been proposed for intraocular surgery. High power lasers, such as YAG lasers, have in the past been positioned outside the eye with their beams focused inside the eye for membrane ablation by direct irradiance. These methods, and proposed methods for using YAG lasers inside the eye, introduce a substantial danger of damaging the eye from the high power light delivered by a YAG laser. A particular danger is that the retina may be irreparably damaged.

One reason a high power YAG laser is desirable for intraocular surgery is because a YAG laser can produce sufficient power to achieve laser induced breakdown (LIB), also called laser induced optical breakdown, which can be a very effective means for puncturing tissue. LIB is a process by which atoms are ionized and a plasma of quasi-free electrons and ions created. The plasma is a superheated mixture of ionized atoms, free electrons and various gases and liquids produced in the process. The ionization is induced by electron absorption of photons and lasts approximately the duration of the pulse creating it. In a liquid, the plasma first expands, where optical absorption produces superheating, further ionization, vaporization of non-ionized liquid and thermal expansion. Second, the plasma collapses, where cooling produces broadband light emission from electron-ion recombination. Third, resulting from the plasma expansion, supersonic shock waves expand from the focal volume. Finally, a cavitation bubble expands and collapses. The cavitation bubble collapse causes the creation of smaller residual bubbles. The combination thermal and mechanical (acoustic) effects are very efficient at disrupting tissue.

LIB occurs by one of two ionization mechanisms, avalanche or multiphoton. Avalanche ionization occurs when a seed electron absorbs photons, accelerates and frees bound electrons by collisional ionization. These electrons in turn accelerate and free more electrons and the process cascades into a volume of plasma. Avalanche ionization is likely to occur in the nanosecond (ns) time regime where the pulse is relatively long, compared to the collisional ionization time, and present in the lens focal region for an extended period of time so that the cascade can propagate. This mechanism is highly impurity dependent. Multiphoton ionization occurs when each bound electron is freed by absorption of multiple photons. Each electron acts independently and no particle interactions are needed. Multiphoton ionization is likely to occur in the femtosecond (fs) time regime and a transition occurs between the two processes in the picosecond (ps) time regime. With multiphoton ionization, electrons are stripped and ions are created simultaneously with very little impurity concentration dependence. Pulse irradiances in the fs regime are sufficiently high to ionize water molecules by multiphoton ionization with little regard for the readily available electron-donation impurities.

LIB has been used effectively in three other types of ophthalmic surgery. These include puncturing the opaque posterior capsule (capsulotomy) after cataract surgery, puncturing the iris to relieve intraocular pressure (iridotomy) in patients with glaucoma, and severing opaque strands within the front (anterior) portion of the vitreous cavity. In these procedures, the laser source is external to the eye and focused by a contact lens placed on the cornea. The optical characteristics of the contact lens determine the point of focus. Because the laser light is focused in the anterior of the eye, lower irradiance in the rear (posterior) segment decreases the damage potential to the retina. External delivery systems for LIB are currently not used in the operating room for vitroretinal (inside the vitreous cavity near the retina) surgery.

The prior art has evaluated several proposed laser techniques for intraocular membrane cutting and removal using high power YAG lasers with fiberoptic focusing for membrane ablation by direct irradiance. As mentioned, a general problem with all such proposed laser treatments is the potential for damage to the underlying retina and retinal pigment epithelium (RPE), both of which may be less than 500 μm posterior to the membrane. Damage can occur from transmitted laser energy which is absorbed in the underlying structures, thermal heating adjacent to the treatment site, gas expansion and movement, or shifting of the plasma formation site. A microfocusing probe, such as proposed by Rol et al. and described in the next paragraph, may decrease retinal damage by providing better localization of plasma (in the case of LIB) or better energy delivery (in the case of direct irradiance) with steeper convergence and thus wider divergence beyond the focal area. Laser wavelength can also be chosen to either or both diminish transmission of energy through the vitreous and diminish retinal and RPE absorption. Pulsed laser output may be utilized for LIB with the potential for less thermal damage adjacent to the treatment site and for plasma shielding from optical breakdown. The use of LIB, however, adds the hazard of shock waves, cavitation effects and gas formation.

P. Rol et al., in "Q-Switched Pulses And Optical Breakdown Generation Through Optical Fibers," *Laser and Light in Ophthalmology*, Vol. 3, No. 3, pp. 213–219, 1990, propose melting the tip of an optical fiber into a microlens to make an intraocular, also called an endocular, surgical probe capable of inducing LIB inside the eye. In tests performed in distilled water, Rol et al. achieved LIB in spite of the reduced beam convergence from a melt-formed microlens at the tip of an optical fiber, as compared to the much more easily obtained LIB obtained from free laser beams converging at large cone angles through larger lenses. Unfortunately, Rol et al. reported a number of difficulties, the most important of which is that the amount of energy available at the fiber end is limited by the damage threshold of the fiber itself. Rol et al. reported that the exit surface of the fiber is often destroyed by the shock wave created in the course of plasma generation. Associated with this problem was the unpredictability of the location of the LIB.

The focusing effect of the melt-formed lens of Rol et al. is the same as that of a traditional lens, in that it depends on the curvature of a lens with a constant refractive index to provide the focusing effect. This, however, introduces a limitation of the focusing effect in the vitreous of the eye or in water due to vitreous and water having higher refractive indexes than air. Other problems with using a melted end of an optical fiber as a lens are the expense involved with the creation of such a lens and the inability to exactly reproduce multiple lens with the same focusing power. Another problem with the melt-formed lens of Rol et al. is that it requires a very high level of laser energy to achieve LIB. This indicates that it is focusing only a small portion of the laser light. Such a melt-formed lens is likely only recollimating the laser light reaching the end of the fiber, and not focusing most of the light to a focal point.

Thus it is seen that there is still a need for an effective and safe laser probe for intraocular surgery that can use laser induced breakdown to sever fibrovascular membranes deep within the eye.

It is, therefore, a principal object of the present invention to provide a microfocusing laser probe for intraocular surgery both sufficiently powerful to produce LIB inside the eye and sufficiently focusable to sever fibrovascular membranes without also damaging either the end of the probe or the retina.

It is a feature of the present invention that it provides a widely divergent beam beyond the focal point, substantially decreasing the risk of damage to the retina and other tissues underlying the membranes to be removed.

It is another feature of the present invention that, although its primary use will be for ophthalmic surgery, it will also be able to be used to deliver focused laser energy to other locations within the human body for medical treatment. Such other locations include the middle ear, the oropharynx, joint cavities and other body cavities reachable via laparoscopic delivery systems.

It is an advantage of the present invention that its construction is straightforward and reproducible.

It is another advantage of the present invention that it does not have to be placed underneath a membrane in order to cut it.

These and other objects, features and advantages of the present invention will become apparent as the description of certain representative embodiments proceeds.

SUMMARY OF THE INVENTION

The present invention provides a new microfocusing laser probe for use in intraocular surgery. The breakthrough discovery of the present invention is that a gradient index (GRIN) lens coupled to a high power laser permits sharply focusing the laser output to a small enough spot size to achieve LIB, yet far enough away from the end of the lens so that the lens is not damaged, and with a wide enough divergence angle past the focal point so that the risk to the retina and other tissues underlying the membranes to be removed is greatly reduced. Another unique discovery of the present invention is that the use of a tapered optical fiber further increases the energy density available at the focal point for achieving LIB.

Accordingly, the present invention is directed to an intraocular laser probe, comprising a laser light source capable of producing sufficient light energy to achieve laser induced breakdown in a preselected liquid, an optical coupler having a first end and a second end, wherein the laser light source is optically connected to the first end of the optical coupler, and a gradient index lens optically connected to the second end of the optical coupler, wherein the focal length of the gradient index lens is such that it will focus light transmitted from the laser light source to a spot small enough to achieve sufficient energy density to produce laser induced breakdown in the preselected liquid, and wherein the spot is far enough from the gradient index lens to prevent damage to the gradient index lens. The laser light source may produce collimated light and the optical coupler may preserve the collimation of collimated light entering the first end of the optical coupler and exiting the second end of the optical coupler. The optical coupler may include an optical fiber. The optical coupler may also include a multi-mode optical fiber. The optical coupler may further include a tapered optical fiber.

The present invention is also directed to a method for surgically removing fibrovascular membranes from within the vitreous cavity of the eye, comprising the steps of providing a laser light source capable of producing light of sufficient energy to achieve laser induced breakdown in vitreous humor, providing an optical coupler having a first end and a second end, wherein the laser light source is optically connected to the first end of the optical coupler, providing a gradient index lens optically connected to the second end of the optical coupler, wherein the focal length of the gradient index lens is such that it will focus light transmitted from the laser light source to a spot small enough to achieve sufficient energy density to produce laser induced breakdown in vitreous humor, and wherein the spot is far enough from the gradient index lens to prevent damage to the gradient index lens, inserting the gradient index lens inside the eye to a position near a fibrovascular membrane desired to be removed, and, after inserting and positioning the lens, turning on the laser light source so that a region of laser induced breakdown occurs at the fibrovascular membrane.

DESCRIPTION OF THE DRAWINGS

The present invention will be more clearly understood from a reading of the following detailed description in conjunction with the accompanying drawings wherein.

DETAILED DESCRIPTION

Figure 1:
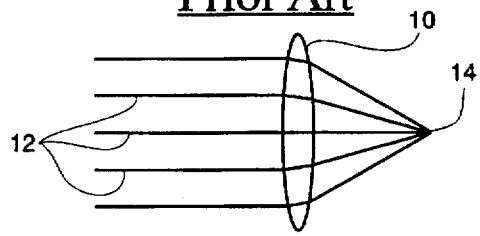
FIG. 1 is a schematic view of a prior art spherical lens showing the well-known focusing of collimated light rays to a focal point.

Referring now to FIG. 1 of the drawings, there is shown a schematic view of a prior art spherical lens 10 illustrating the well-known focusing of collimated light rays 12 to a focal point 14.

Figure 2:
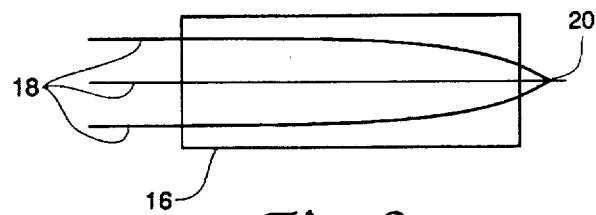
FIG. 2 is a schematic view of a prior art gradient index lens showing the focusing of collimated light rays to a focal point.

FIG. 2 shows a schematic view of a prior art optical gradient index lens 16 showing focusing of light rays 18 to a focal point 20. Gradient index lens 16 focuses light using a refractive index that decreases radially from the optical axis of lens 16. This allows light traveling in a region with a lower refractive index to travel at a greater speed, resulting in a bending of light rays toward focal point 20. Gradient index lens 16 is superior to a traditional lens for use in eye surgeries due to its smaller size. Another advantage of gradient index lens 16 is its superior focusing capability over a traditional lens in water or vitreous. Gradient index lens 16 focuses by relying on a refractive index which decreases radially outward from its axis, thereby internally bending laser light rays 18, as opposed to a traditional lens which relies on refraction at the interface between the traditional lens and an external media.

Additional background and details for the following described microfocusing laser probes are included in C. A. Toth et al., "Gradient Index (GRIN) Lens Multimode Fiber Probe for Laser Induced Breakdown in the Eye," *Proceedings of Ophthalmic Technologies IV*, Vol. 2126, pp. 291–304, 1994; and, in C. E. Clary, "Intra-Ocular Laser Surgical Probe (ILSP) for Vitreous Micro-Surgery," unpublished Final Report for Graduate Student Research Program, University of Alabama at Birmingham, pp. 6-1–6-20, August, 1994, both of which are incorporated by reference into this Detailed Description. A copy of the unpublished Final Report has been filed with the patent application for the present invention.

Figure 3:
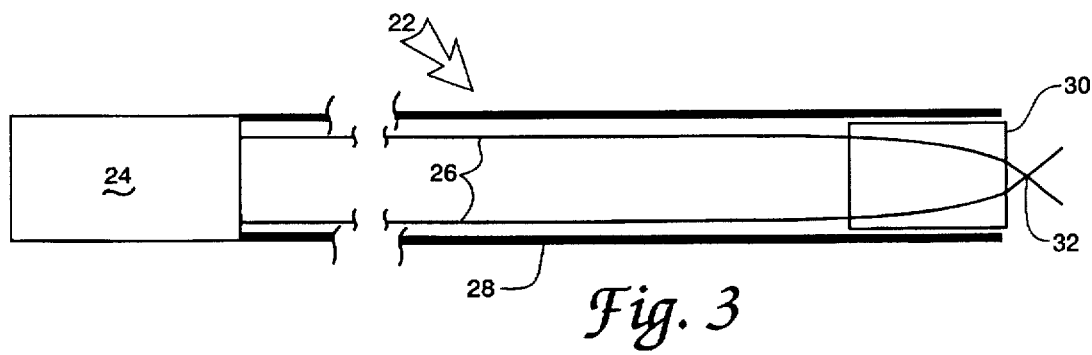
FIG. 3 is a simplified cross-sectional side view of an intraocular microfocusing laser probe according to the teachings of the present invention showing the direct delivery of collimated laser light to a gradient index lens.

FIG. 3 is a simplified cross-sectional side view of an intraocular microfocusing laser probe 22 according to the teachings of the present invention. Laser probe 22 includes a source 24 of collimated laser light 26, an open transmission line or optical coupler 28 and a gradient index lens 30. Laser light source 24 is a high power Nd:YAG laser emitting 10 ns pulses at 1064 nm. A pulsed laser light source is needed to achieve LIB. Other lasers, pulse durations and wavelengths may be chosen as discussed in the two articles incorporated by reference. Open transmission line 28 delivers collimated laser light 26 to gradient index lens 30 with the collimation substantially preserved. Open transmission line 28 is constructed out of surgical stainless steel or other material suitable for surgical instruments. Laser probe 22 preferably will include, if necessary, an optical element to recollimate laser light 26 to the same diameter as the back of gradient index lens 30.

Gradient index lens 30 sharply focuses laser light 26 at a focal point 32 so that laser light 26 will diverge widely past focal point 32 and decrease to safe levels the energy density of remaining laser light that strikes the retina during eye surgery. This allows, first, intraocular microfocusing laser probe 22 to be used near the retinal surface for removal of fibrovascular membranes without damage to the retina or retinal pigment epithelium. Second, the use of a GRIN lens allows focal point 32 to be chosen to be at sufficient distance from the end of lens 30 so that the resulting LIB will not also damage the end of lens 30. Third, incoming laser light 26 from high power laser 24 can now be sufficiently concentrated inside the eye with a probe small enough to fit inside the eye so that the resulting energy density at focal point 32 is enough to achieve LIB. A particular advantage of the choice of a gradient index lens over the prior art is that it, for the first time, satisfies all three of these necessary objects for successful intraocular surgical removal of fibrovascular membranes from inside the vitreous cavity.

Figure 4:
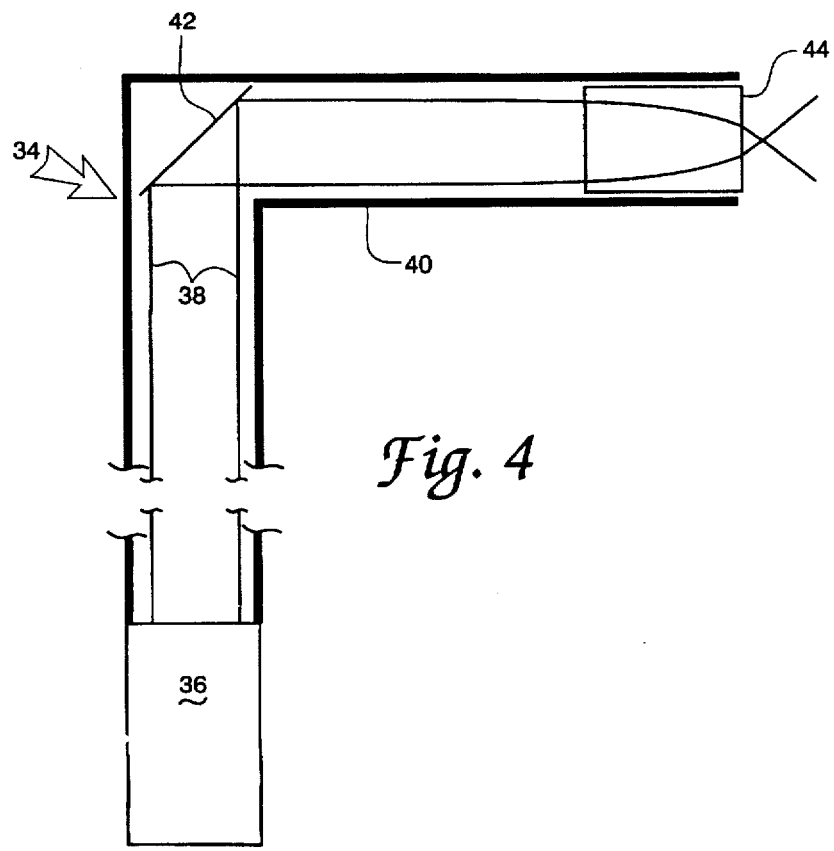
FIG. 4 is a simplified cross-sectional side view of the intraocular microfocusing laser probe of FIG. 3 showing its modification to an articulated microfocusing laser probe.

FIG. 4 shows a very simplified view of an intraocular microfocusing laser probe 34 which is the intraocular microfocusing laser probe of FIG. 3 modified to allow articulation for use in eye surgery. Laser probe 34 includes a source 36 of collimated laser light 38, an open transmission line or optical coupler 40, an optical mirror 42 and a gradient index lens 44. Optical mirror 42 articulates open transmission line 40 while preserving the collimation of laser light 38. The articulation of intraocular microfocusing laser probe 34 increases maneuverability and allows laser source 36 to be positioned in a convenient location during eye surgery. Those of ordinary skill in the art will readily be able to further articulate open transmission line 40 by the addition of other conventional optical elements.

Figure 5:
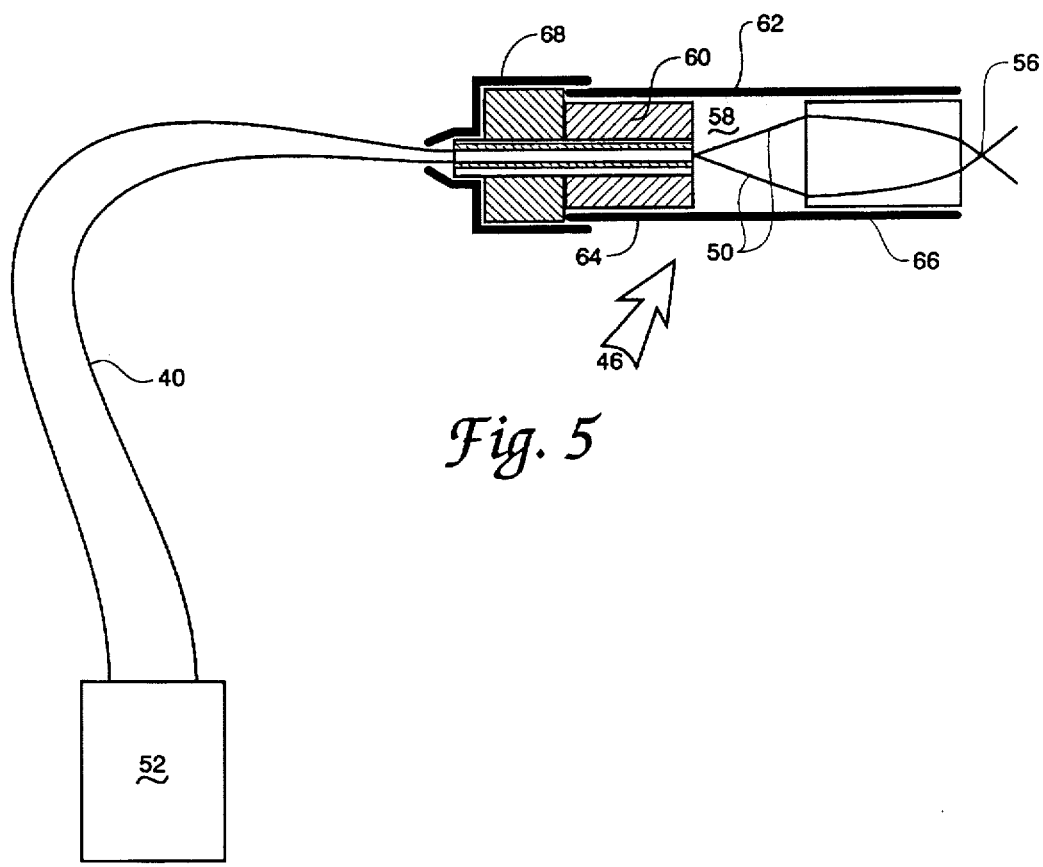
FIG. 5 is a simplified partially cross-sectional side view of another intraocular microfocusing laser probe according to the teachings of the present invention showing the use of a tapered optical fiber for delivering laser light from a high power laser to a gradient index lens; and, FIG. 6 is a partially cross-sectional and partially phantom view of a laser delivery probe according to the teachings of the present invention showing its use inside an eye during surgery.

FIG. 5 shows another intraocular microfocusing laser probe 46 according to the teachings of the present invention. Laser probe 46 uses a multimode optical fiber 48 to deliver laser light 50 from a conventional high power surgical laser 52 to a gradient index lens 54. Optical fiber 48 is tapered to concentrate more energy from laser 52 to gradient index lens 54 to insure sufficient energy density at a focal point 56 to achieve LIB. The taper is exaggerated in this view for clarity. There is an air gap 58 between the end of optical fiber 48 and the back of gradient index lens 54. Air gap 58 couples the output of optical fiber 48 to the entire face of gradient index lens 54 in a more uniform pattern. This allows more power to be transmitted into gradient index lens 54.

Optical fiber 48 terminates in a surgical stainless steel inner ferrule 60 and is polished according to standard procedures for terminating fibers. A surgical stainless steel outer ferrule 62 has two small holes 64 and 66 for inserting glue to hold inner ferrule 60 and gradient index lens 54 in place. The glue and a length of heat shrink tubing 68 seal the tube and make it airtight.

Gradient index lens 54, a SELFOC brand gradient index lens available from Nippon Sheet Glass, Inc., has a diameter of 1.8 mm and a length of 4.4 mm. Air gap 58 is 4.1 mm wide. Optical fiber 48 terminates at a core diameter of 0.1 mm. In this embodiment, the optical characteristics of gradient index lens 54 are chosen to focus laser light 50 to a focal point 56 1.23 mm from the end of lens 54.

Figure 6:
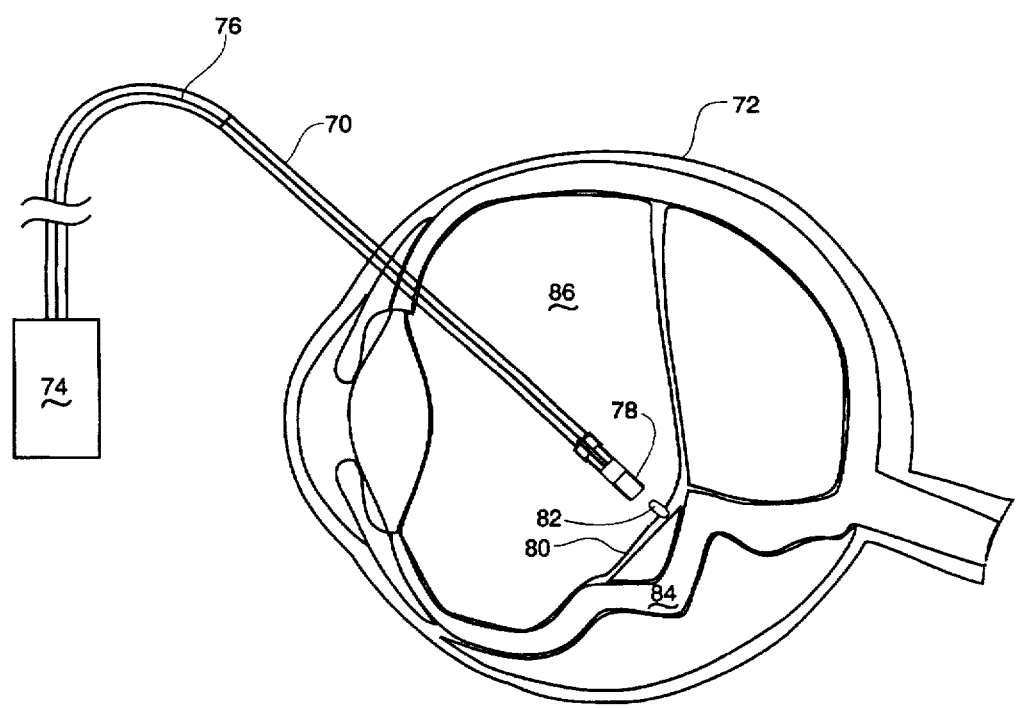

FIG. 6 is a partially cross-sectional and partially phantom view of a laser delivery probe 70 according to the teachings of the present invention showing its use inside an eye 72 during surgery. Laser delivery probe 70 includes a high power laser 74, a tapered optical fiber 76 and a gradient index lens 78.

Laser delivery probe 70 will be inserted into the eye through a sclerotomy incision and positioned near to, but not touching, a fibrovascular membrane 80 by known means, such as surgical microscope or endoscopic viewing. High power laser 74 will deliver energy at discrete levels above the breakdown threshold to achieve a region 82 of LIB at fibrovascular membrane 80, but below energy levels which would damage gradient index lens 78. Gradient index lens 78 will sharply focus the laser light, so that the laser light will widely diverge beyond the end of the probe, thereby not damaging a detached retina 84. Laser probe 70 will be moved along fibrovascular membrane 80 until it is completely severed from the vitreous 86 or the retina 84. Membrane 80 will be removed using a conventional suction probe for ophthalmic surgery. Laser delivery probe 70 may include additional infusion and aspiration channels. For example, an aspiration channel may be added which would hold the membrane at the LIB focal distance from the tip of the probe for efficient cutting. During ophthalmic surgery, the location of all probes and tissue cutting would be observed through the operating microscope or endoscopic viewing system if the media is not clear. Because the optical fiber is multimodal, an endoscopic viewing system can be incorporated into the probe.

The disclosed laser surgical probe successfully demonstrates the advantages of combining a gradient index lens with a high power laser for intraocular surgery. Although the disclosed surgical probe is specialized, its teachings will find application in other areas where it will be desirable to achieve high light energy densities inside a small space.

To ensure that sufficient energy density can be focused inside the eye to achieve LIB in the vitreous humor, the disclosed invention uses either collimated light from a conventional high power surgical laser delivered to the back of a gradient index lens with its collimation preserved, or a tapered optical fiber to concentrate more laser energy at the back of the gradient index lens. Those with skill in the art of the invention will see that other types and sizes of optical fibers, and other laser-fiber combinations, may also concentrate enough laser energy at the rear of the gradient index lens to achieve LIB. These and other modifications to the invention as described may be made, as might occur to one with skill in the field of the invention, within the intended scope of the claims. Therefore, all embodiments contemplated have not been shown in complete detail. Similarly, other embodiments may be developed without departing from the spirit of the invention or from the scope of the claims.

We claim:

1. A laser probe, comprising:
   (a) a laser light source capable of producing light of sufficient energy to achieve laser-induced breakdown in a preselected liquid;
   (b) an optical coupler including a tapered optical fiber and having a first end and a second end, wherein the laser light source is optically connected to the first end of the optical coupler; and,
   (c) a gradient index lens optically connected to the second end of the optical coupler, wherein the focal length of the gradient index lens is such that it will focus light transmitted from the laser light source to a spot small enough to achieve sufficient energy density to produce laser-induced breakdown in the preselected liquid, and wherein the spot is far enough from the gradient index lens to prevent damage to the gradient index lens.

2. A method for surgically removing fibrovascular membranes from within the vitreous cavity of the eye; comprising the steps of:
   (a) providing a laser light source capable of producing light of sufficient energy to achieve laser-induced breakdown in vitreous humor;
   (b) providing an optical coupler including a tapered optical fiber and having a first end and a second end, wherein the laser light source is optically connected to the first end of the optical coupler;
   (c) providing a gradient index lens optically connected to the second end of the optical coupler, wherein the focal length of the gradient index lens is such that it will focus light transmitted from the laser light source to a spot small enough to achieve sufficient energy density to produce laser-induced breakdown in vitreous humor, and wherein the spot is far enough from the gradient index lens to prevent damage to the gradient index lens;
   (d) inserting the gradient index lens inside the eye to a position near a fibrovascular membrane desired to be removed; and,
   (e) after performing step (d), turning on the laser light source so that a region of laser induced breakdown occurs at the fibrovascular membrane.

3. A method for surgically removing an area of tissue from inside a body; comprising the steps of:
   (a) providing a laser light source capable of producing light of sufficient energy to achieve laser-induced breakdown in a preselected bodily fluid;
   (b) providing an optical coupler including a tapered optical fiber and having a first end and a second end, wherein the laser light source is optically connected to the first end of the optical coupler;
   (c) providing a gradient index lens optically connected to the second end of the optical coupler, wherein the focal length of the gradient index lens is such that it will focus light transmitted from the laser light source to a spot small enough to achieve sufficient energy density to produce laser-induced breakdown in the preselected bodily fluid, and wherein the spot is far enough from the gradient index lens to prevent damage to the gradient index lens;
   (d) inserting the gradient index lens inside the body to a position near the area of tissue to be surgically removed; and,
   (e) after performing step (d), turning on the laser light source so that a region of laser-induced breakdown occurs at the area of tissue.

4. A laser probe, comprising:
   (a) a laser light source capable of producing light of sufficient energy to achieve laser-induced breakdown in a preselected liquid;
   (b) an optical coupler including means for concentrating light and having a first end and a second end, wherein the laser light source is optically connected to the first end of the optical coupler; and,
   (c) a gradient index lens optically connected to the second end of the optical coupler, wherein the focal length of the gradient index lens is such that it will focus light transmitted from the laser light source to a spot small enough to achieve sufficient energy density to produce laser-induced breakdown in the preselected liquid, and wherein the spot is far enough from the gradient index lens to prevent damage to the gradient index lens.

5. A method for surgically removing fibrovascular membranes from within the vitreous cavity of the eye; comprising the steps of:
   (a) providing a laser light source capable of producing light of sufficient energy to achieve laser-induced breakdown in vitreous humor;
   (b) providing an optical coupler including means for concentrating light and having a first end and a second end, wherein the laser light source is optically connected to the first end of the optical coupler;
   (c) providing a gradient index lens optically connected to the second end of the optical coupler, wherein the focal length of the gradient index lens is such that it will focus light transmitted from the laser light source to a spot small enough to achieve sufficient energy density to produce laser-induced breakdown in vitreous humor, and wherein the spot is far enough from the gradient index lens to prevent damage to the gradient index lens;
   (d) inserting the gradient index lens inside the eye to a position near a fibrovascular membrane desired to be removed; and,
   (e) after performing step (d), turning on the laser light source so that a region of laser induced breakdown occurs at the fibrovascular membrane.

6. A method for surgically removing an area of tissue from inside a body; comprising the steps of:

(a) providing a laser light source capable of producing light of sufficient energy to achieve laser-induced breakdown in a preselected bodily fluid;

(b) providing an optical coupler including means for concentrating light and having a first end and a second end, wherein the laser light source is optically connected to the first end of the optical coupler;

(c) providing a gradient index lens optically connected to the second end of the optical coupler, wherein the focal length of the gradient index lens is such that it will focus light transmitted from the laser light source to a spot small enough to achieve sufficient energy density to produce laser-induced breakdown in the preselected bodily fluid, and wherein the spot is far enough from the gradient index lens to prevent damage to the gradient index lens;

(d) inserting the gradient index lens inside the body to a position near the area of tissue to be surgically removed; and, (e) after performing step (d), turning on the laser light source so that a region of laser-induced breakdown occurs at the area of tissue.

* * * * *